US00PP09580P

United States Patent [19]

Trees

[11] Patent Number: Plant 9,580

[45] Date of Patent: Jun. 11, 1996

[54] GERANIUM PLANT NAMED 'BFP-837 SCARLET'

[75] Inventor: Scott C. Trees, Arroyo Grande, Calif.

[73] Assignee: Geo. J. Ball, Inc., West Chicago, Ill.

[21] Appl. No.: 443,666

[22] Filed: May 18, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

The new and distinct *Pelargonium×hortorum* cultivar named 'BFP–837 Scarlet' is provided. This new Zonal Geranium was the result of a controlled breeding program wherein the a plant designated 11185A (non-Patented in the United States) was pollinated by a plant designated PAS 186-4-4-1 (non-patented in the United States). The new cultivar forms attractive large semi-double scarlet florets commonly with a darker area on two petals of each floret. Dark green foliage is well retained during shipment. A medium self-branching growth habit is exhibited that does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-837 Scarlet'.

The new cultivar is a product of a planned breeding program which had the objective of the creation of a Geranium cultivar that exhibits uniform flowers, dark green foliage, a medium self-branching growth habit that requires no growth regulator, a propensity for rapid rooting, and stable foliage coloration during shipment.

The breeding program that resulted in the production of the new cultivar of the present invention was carred out in a controlled environment during 1992 at Arroyo Grande, Calif., U.S.A. The female parent (i.e., seed parent) was a plant designated 11185A (non-patented in the United States) which exhibits single bright rose florets with medium green foliage. The male parent (i.e., pollen parent) was a plant designated PAS 186-4-4-1 (non-patented in the United States) which exhibits semi-double coral florets with dark green foliage. The parentage of the new 'BFP-837 Scarlet' cultivar can be summarized as follows:

11185A×PAS 186-4-4-1.

'BFP-837 Scarlet' was discovered and selected during 1992 as a highly distinctive flowering plant from among the progeny of the stated cross at Arroyo Grande, Calif., U.S.A. This plant was initially designated BFP-837.

It was found that the new cultivar of the present invention (a) exhibits attractive large semi-double scarlet florest commonly having a darker area on two petals of each floret,
(b) forms attractive dark green foliage, and
(c) exhibits a medium self-branching growth habit in the absence of a growth regulator.

When plant material of the 'BFP-837 l Scarlet' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of 'BFP-837 Scarlet' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'BFP-837 Scarlet' cultivar is fixed and is retained through successive generations of such asexual reproduction.

The new 'BFP-837 Scarlet' cultivar has not been observed under all possible environmental conditions. Accordingly, the described phenotype may vary somewhat with variations in the environment, such as temperature, light intensity, and day length.

Of the many commercial cultivars, the 'BSR-232 Light Scarlet' cultivar (U.S. Plant Pat. No. 8,285) is considered to be the most similar to the new cultivar of the present invention. When the new cultivar of the present invention is compared to the 'BSR-232 Light Scarlet' cultivar, it is found that the 'BFP-837 Scarlet' cultivar exhibits a less compact growth habit (e.g., approximately 29 to 31 cm. in height vs. approximately 23 to 28 cm.), generally larger florets (e.g., approximately 5.6 to 5.9 cm. vs. approximately 4.2 to 4.5 cm.), and generally more petaloids (e.g., approximately 4 to 5 vs. approximately 2 to 4). The 'BFP-837 Scarlet' cultivar additionally exhibits longer peduncles, longer pedicels, and larger leaves as specified in greater detail hereafter.

The new cultivar of the present invention is being marketed by Geo. J. Ball, Inc. under the Showcase trademark.

BRIEF DESCRIPTION OF THE PHOTOGRAPHS

The accompanying photographs show the new 'BFP-837 Scarlet' cultivar with colors being as nearly true as it is reasonably possible to make the same in color illustrations of this character. The plants were being grown in greenhouses at West Chicago, Ill. U.S.A.

DETAILED DESCRIPTION

Figure 1:
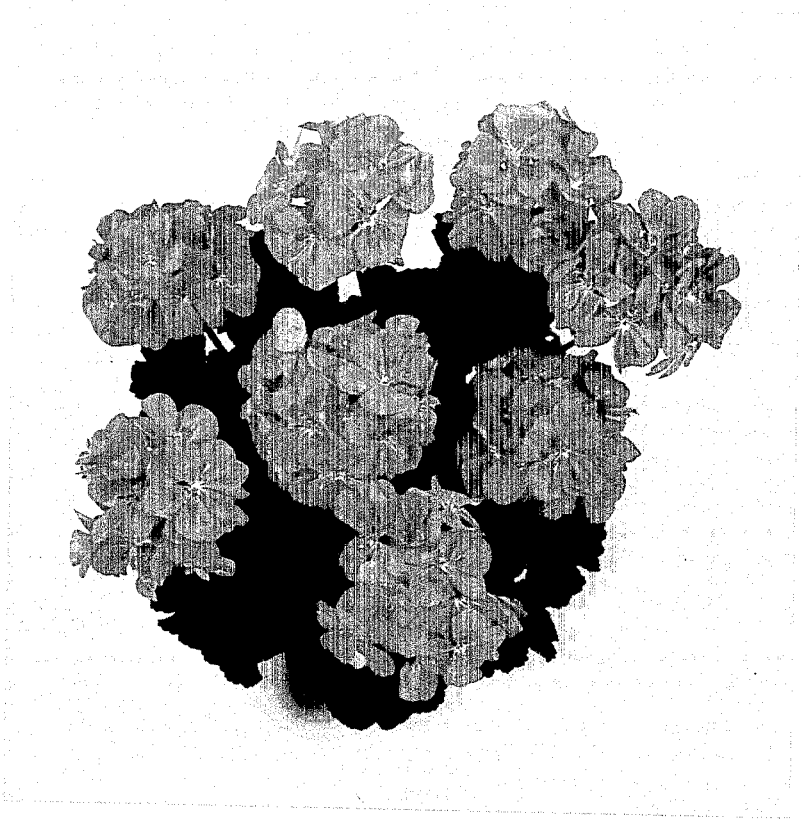
FIG. 1 illustrates the general appearance of an overall plant as seen primarily from above.
Figure 2:
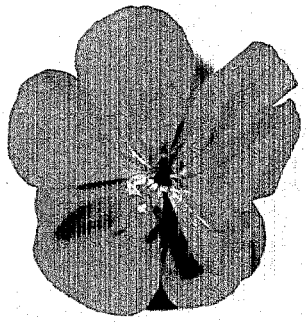
FIG. 2 illustrates the general appearance of a typical floret.

The following observations, measurements and comparisons describe plants grown in Ball FloraPlant's greenhouses located at West Chicago, Ill., U.S.A., under conditions which approximate those generally used in commercial practice. In the following description, color references are made to the R.H.S. Colour Chart of The Royal Horticultural Society, London, England. The color values were determined between 9:00 and 9:30 a.m. on Dec. 27, 1994, under natural light conditions of 2,000 footcandles.

Classification:

*Botanical.*—*Pelargonium×hortorum* Bailey, cv. 'BFP-837 Scarlet'.

*Commerical.*—Zonal Geranium.

Inflorescence

A. Umbel:

*Average diameter.*—Approximately 10.2 to 11.5 cm. compared to approximately 10.0 to 11.0 cm. for the 'BSR-232 Light Scarlet' cultivar (U.S. Plant Pat. No. 8285).

*Average depth.*—Approximately 6.0 to 7.0 cm. compared to approximately 5.5 to 6.0 cm. for the 'BSR-232 Light Scarlet' cultiavr.

*Peduncle length.*—Approximately 18.0 to 20.0 cm. compared to approximately 12.5 to 17.0 cm. for the 'BSR-232 Light Scarlet' cultivar.

Pedicel length.—Approximately 3.8 to 4.8 cm. compared to approximately 3.0 to 3.6 cm. for the 'BSR-232 Light Scarlet ' cultivar.

*Number of umbels/plant.*—When grown in a 10 cm. pot at 9 weeks after the sticking of a rooted cutting, there commonly are approximately 3 to 4 umbels per plant. The 'BSR-232 Light Scarlet' cultivar commonly forms approximately 2 to 5 umbels per plant.

*Number of florets/umbel.*—When grown in 10 cm. pots at 9 weeks, approximately 21 to 28 florets per umbel commonly are formed. This compares to approximately 25 to 37 florets per umbel for the 'BSR-232 Light Scarlet' cultivar under the same growing conditions.

B. Corolla:

*Average diameter.*—Approximately 5.6 to 5.9 cm. compared to approximately 4.2 to 4.5 cm. for the 'BSR-232 Light Scarlet' cultivar.

*Form.*—Both the 'BFP-837 Scarlet' cultivar and the 'BSR-232 Light Scarlet' cultivar are semi-double with petaloids, and commonly possess 5 petals per floret.

*Number of petaloids.*—Commonly forms 4 to 5 petaloids per floret whereas the 'BRS-232 Light Scarlet' cultivar commonly possesses 2 to 4 petaloids per floret.

*Color.*—General tonality from a distance of three meters: Red. Adaxial: Red Group 43B with approximately two petals per floret having a darker area of the Red Group 43A. This compares to Red Group 44B for the 'BFP-232 Light Scarlet' cultivar. Abaxial: Red Group 40B. This compares to Orange-Red Group 33A for the 'BSR-232 Light Scarlet' cultivar.

C. Bud:

*Shape.*—Oval-rounded.

*Color.*—Adaxial: Red Group 40A compared to Red Group 44B for the 'BSR-232 Light Scarlet' cultivar. Abaxial: Red Group 40B compared to Orange-Red Group 33A for the 'BSR-232 Light Scarlet' cultivar.

D. Reproductive organs:

*Androecium.*—The anthers are commonly approximately 2.5 mm. in length. The pollen color commonly is Orange-Red Group 31B for both the 'BFP-837 Scarlet' cultivar and the 'BSR-232 Light Scarlet' cultivar. The filaments are approximately 9.0 to 12.0 mm. in length.

*Gynoecium.*—The pistil length commonly is approximately 9.0 to 10.0 mm. There is a single stigma which commonly has a length of approximately 4.0 mm. which commonly branches into 5 parts, and the style length is approximately 4.5 to 5.0 mm.

*Fertility.*—Commonly does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

Plant

A. Foliage: Dark green.

*Form.*—Reniform, with cordate base.

*Margin.*—Crenate.

*Color.*—Adaxial: Green Group 139A for both the 'BFP-837 Scarlet' cultivar and the 'BSR-232 Light Scarlet' cultivar. Abaxial: Green Group 137C for both the 'BFP-837 Scarlet' cultivar and the 'BSR-232 Light Scarlet' cultivar.

*Size.*—Approximately 9.0 to 11.5 cm. at the widest point and approximately 7.5 to 10.0 cm. at the narrowest point. This compares to approximately 8.2 to 9.4 cm. at the widest point and approximately 6.6 to 7.0 cm. at the narrowest point for the 'BSR-232 Light Scarlet' cultivar.

B. General appearance and form:

*Internode length.*—Commonly varies from approximately 1.5 to 2.5 cm. This compares to approximately 1.5 to 2.5 cm. for the 'BSR-232 Light Scarlet' cultivar.

Branching pattern.—Freely basal branching. No pinching is required to obtain self-branching. A vigorous self-branching growth habit is observed in the absence of a growth regulator.

*Height.*—Approximately 29 to 31 cm. above a 10 cm. pot at 9 weeks under standard greenhouse conditions. This compares to approximately 23 to 28 cm. for the 'BSR-232 Light Scarlet' cultivar.

I claim:

1. A new and distinct Geranium cultivar named 'BFP-837 Scarlet', substantially as herein shown and described, which:

(a) exhibits attractive large semi-double scarlet florets commonly having a darker area on two petals of each floret, (b) forms attractive dark green foliage, and (c) exhibits a medium self-branching growth habit in the absence of a growth regulator.

* * * * *